United States Patent
Mialhe

(10) Patent No.: US 7,445,623 B2
(45) Date of Patent: Nov. 4, 2008

(54) OCCLUSIVE DEVICE FOR MEDICAL OR SURGICAL USE

(76) Inventor: Claude Mialhe, 292 Chemin de la Sirene, Draguignan (FR) 83300

( * ) Notice: Subject to any disclaimer, the term of this patent is extended or adjusted under 35 U.S.C. 154(b) by 604 days.

(21) Appl. No.: 10/535,148

(22) PCT Filed: Oct. 15, 2003

(86) PCT No.: PCT/FR03/50093

§ 371 (c)(1),
(2), (4) Date: May 16, 2005

(87) PCT Pub. No.: WO2004/045419

PCT Pub. Date: Jun. 3, 2004

(65) Prior Publication Data

US 2006/0052804 A1 Mar. 9, 2006

(30) Foreign Application Priority Data

Nov. 15, 2002 (FR) .................................. 02 14290

(51) Int. Cl.
*A61B 17/08* (2006.01)
(52) U.S. Cl. .................... 606/157; 606/158; 623/14.13; 600/30
(58) Field of Classification Search .................. 600/184; 606/157, 158, 200, 213, 127, 151, 198
See application file for complete search history.

(56) References Cited

U.S. PATENT DOCUMENTS

| | | | | |
|---|---|---|---|---|
| 4,401,107 A * | 8/1983 | Haber et al. | ................... | 600/30 |
| 4,580,573 A | 4/1986 | Quinn | | |
| 4,705,518 A * | 11/1987 | Baker et al. | ............... | 623/14.13 |
| 4,721,030 A * | 1/1988 | Paynter | ......................... | 92/92 |
| 5,112,324 A * | 5/1992 | Wallace | ....................... | 604/349 |
| 5,197,984 A * | 3/1993 | Kedem | ..................... | 623/14.13 |
| 5,957,913 A * | 9/1999 | de la Torre et al. | ............... | 606/1 |
| 6,063,113 A * | 5/2000 | Kavteladze et al. | ........ | 623/1.15 |
| 6,096,052 A * | 8/2000 | Callister et al. | ............. | 606/157 |
| 6,398,807 B1 * | 6/2002 | Chouinard et al. | ......... | 623/1.35 |
| 6,432,116 B1 * | 8/2002 | Callister et al. | ............. | 606/157 |
| 6,461,320 B1 * | 10/2002 | Yencho et al. | .................. | 604/8 |
| 6,641,593 B1 * | 11/2003 | Schaller et al. | ............. | 606/157 |
| 6,685,738 B2 * | 2/2004 | Chouinard et al. | ......... | 623/1.15 |
| 2002/0029051 A1 * | 3/2002 | Callister et al. | ............. | 606/157 |
| 2002/0143349 A1 * | 10/2002 | Gifford et al. | ............... | 606/157 |
| 2002/0147457 A1 * | 10/2002 | Rousseau | ..................... | 606/157 |
| 2003/0040772 A1 * | 2/2003 | Hyodoh et al. | .............. | 606/200 |
| 2003/0139802 A1 * | 7/2003 | Wulfman et al. | ........... | 623/1.15 |
| 2003/0153935 A1 * | 8/2003 | Mialhe | ........................ | 606/157 |

(Continued)

FOREIGN PATENT DOCUMENTS

EP 0 834 279 4/1998

(Continued)

*Primary Examiner*—Kevin T Truong
*Assistant Examiner*—Erin Colello
(74) *Attorney, Agent, or Firm*—Young & Thompson

(57) ABSTRACT

The present invention relates to an occlusive device for medical or surgical use, having a hollow, axial twist deformable cylindrical element (1) designed to create a striction zone, and obturation elements (2a, 2b) integral to the inner wall of the cylindrical element, allowing a passage and arranged in such a manner as to be pressed against each other to block the passage when the cylindrical element (1) is twisted.

18 Claims, 4 Drawing Sheets

U.S. PATENT DOCUMENTS

| | | | |
|---|---|---|---|
| 2003/0195530 A1* | 10/2003 | Thill | 606/151 |
| 2005/0096750 A1* | 5/2005 | Kagan et al. | 623/23.65 |
| 2006/0020286 A1* | 1/2006 | Niermann | 606/200 |
| 2006/0212055 A1* | 9/2006 | Karabey et al. | 606/158 |
| 2006/0224183 A1* | 10/2006 | Freudenthal | 606/213 |
| 2007/0276415 A1* | 11/2007 | Kladakis et al. | 606/151 |

FOREIGN PATENT DOCUMENTS

| | | |
|---|---|---|
| EP | 864300 A1 * | 9/1998 |
| WO | WO 02/19926 | 3/2002 |
| WO | WO 0219926 A1 * | 3/2002 |
| WO | WO 02/32320 | 4/2002 |

* cited by examiner

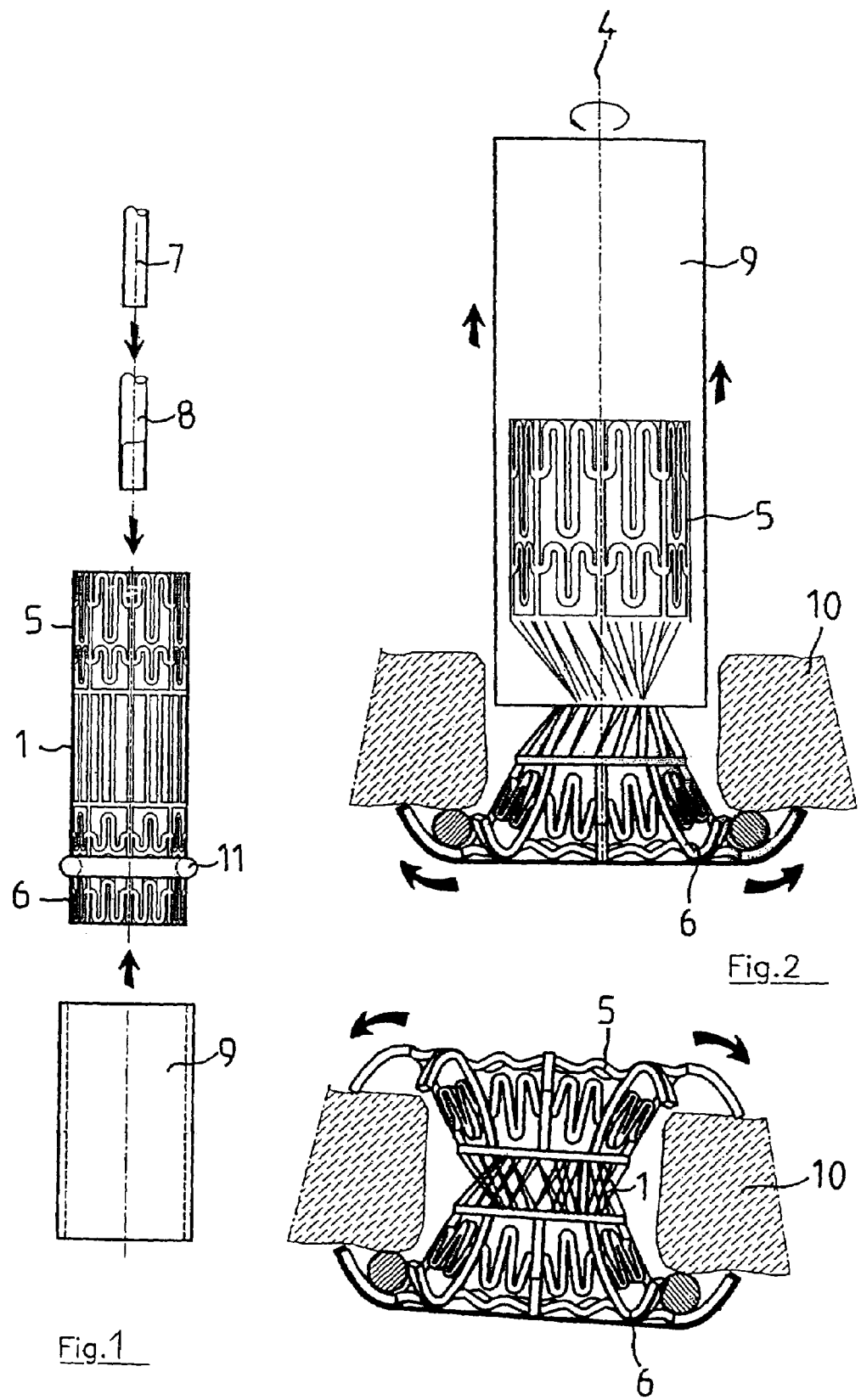

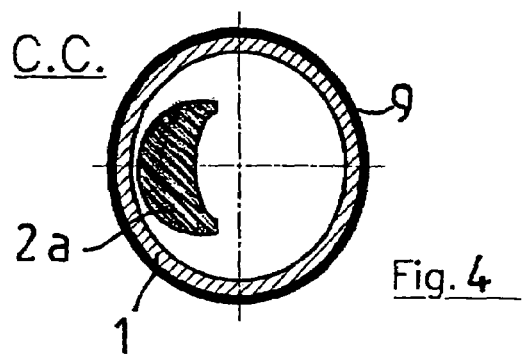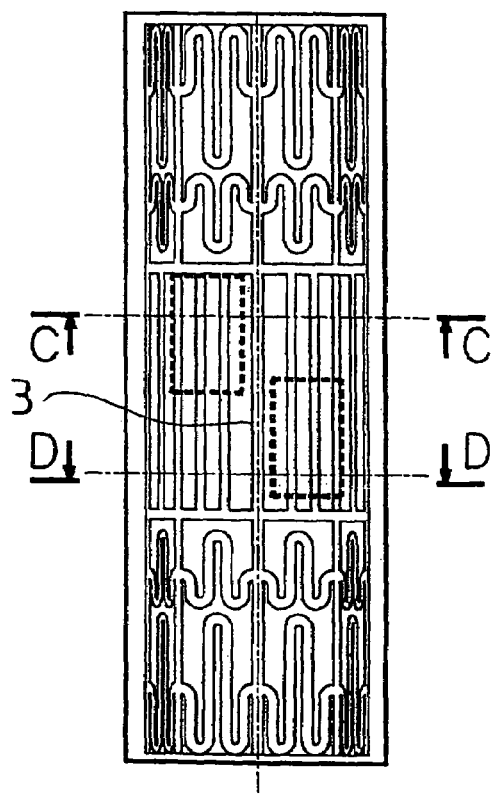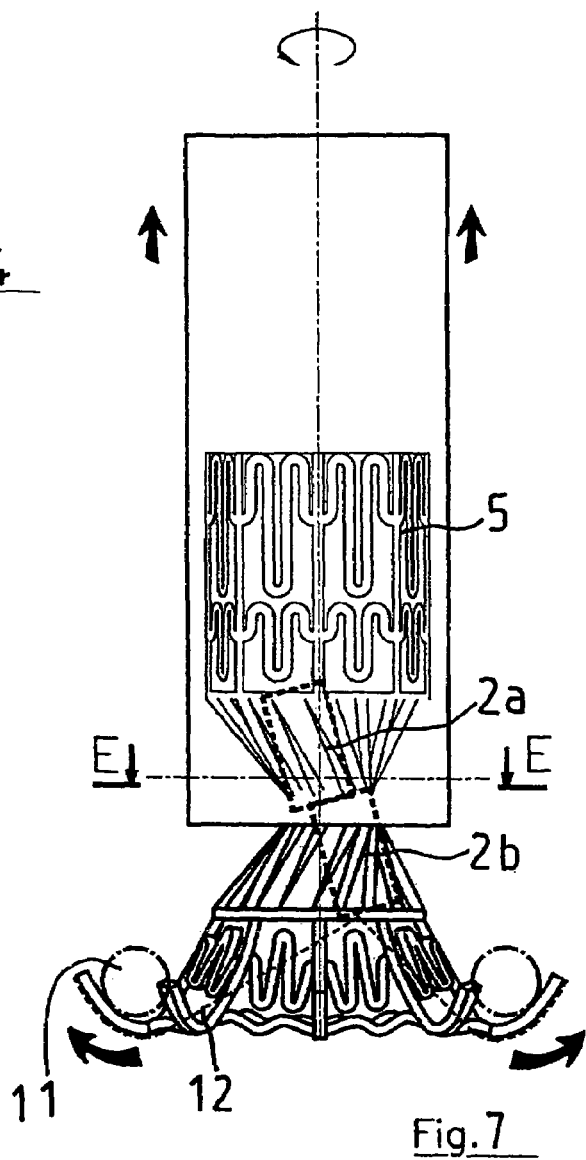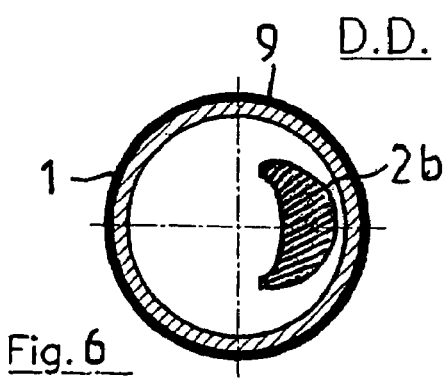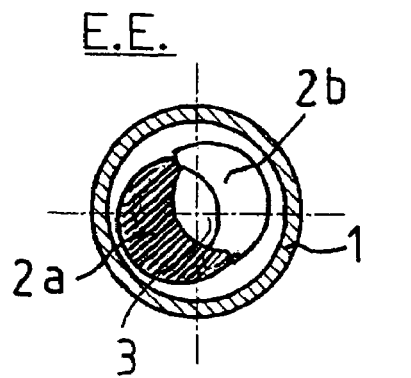

F.F.

OCCLUSIVE DEVICE FOR MEDICAL OR SURGICAL USE

The present invention relates to an occlusive device for medical or surgical use, and to a vascular occlusion device and a valve for surgical or medical instruments.

The invention will find applications, in particular, in the field of manufacture and use of occlusive prostheses for all types of vessels in humans or animals, prostheses that may also include transparietal and endovascular devices.

The invention also relates to the field of surgical or medical instruments and in particular introducer type instruments that may be used during endovascular surgery, including percutaneous and/or transparietal operations, which require the presence of obturation elements able to ensure that the introducer is sealed.

The quality of the occlusion is a constant problem according to the current state of the art, both in the field of vascular prostheses and for the creation of valves.

Document WO-A-0219926 relates to a vascular occlusion device comprised of two expanding elements for attachment by support against two portions of the vessel's wall, along with an intermediate section that can be twisted to an adjustable degree according to the relative position of the two expanding elements. A maximum striction area is thus created, defining the degree of occlusion.

According to this document, total or partial obturation is achieved by means of the twisting deformation of an element.

This technique provides a great ease of intervention and the ability to fine tine the degree of obturation.

There is, however, a need to further improve the sealing provided by this type of device.

The present invention provides a solution to this problem by adjoining other occlusion elements able to cooperate with the twist deformable element.

Most preferably, but not in a limiting manner, the invention also presents the advantage of offering additional sealing possibilities in the form of seals that can be applied to the wall of a vessel, possibly in combination with an obturation web.

Other purposes and advantages shall appear during the following description of a preferred embodiment of the invention, which is nevertheless not limiting.

The present invention relates to an occlusive device for medical or surgical use, comprising a hollow, axial twist deformable cylindrical element designed to create a striction zone, characterised by the fact that it comprises two obturation elements integral to the inner wall of the cylindrical element, allowing a passage and arranged in such a manner as to be pressed against each other to block the passage when the cylindrical element is twisted.

In the preferred embodiments, this occlusive device is such that:
the two obturation elements are integral to two distinct areas of the length of the cylindrical element.
the obturation elements have a crescent-shaped cross section.
the obturation elements are integral to two diametrically opposite areas of the wall of the cylindrical element.
the obturation elements are made from a polymer material.
there are two end parts, surrounding the cylindrical element and whose angular position determines the torsion of said cylindrical element.
The cylindrical element has a circular cross section.
the obturation elements are applied one against each other by means of one of their lateral surfaces.

The invention also relates to a vascular occlusion device characterised by the fact that it comprises an occlusive device according to the invention.

This vascular occlusion device may advantageously be presented according to the following variants:
it possesses two end parts, surrounding the cylindrical element and whose relative angular position determines the torsion of said cylindrical element, said end parts possessing means of attachment to the wall of a vessel.
the attachment systems are expanding elements.
it possesses a seal on the outer surface of at least one of the expanding elements, said seal being appropriate for application to the wall of a vessel.
it presents a peripheral obturation web extending from one end of at least one obturation element to the edge of the corresponding expanding element.
it possesses a removable guide oriented according to the axis of the cylindrical element and crossing the passage.
it possesses a removable sheath inserted between the wall of the obturation elements and the external wall of the guide.
it comprises a removable sleeve surrounding the occlusive device.

The invention also relates to a valve for surgical or medical instruments comprising a closeable passage and characterised by the fact that it comprises an occlusive device according to the invention.

The valve is preferably such that the cylindrical element can be twisted by means of two rings, each one integral to an end of the cylindrical element.

The appended drawings are given as an example and do not limit the invention. They represent only one embodiment of the invention and allow it to be easily understood.

FIG. 1 is a general view of the device concerned by the invention for a vascular occlusion application.

FIG. 2 illustrates a step in the transparietal implementation of a vascular occlusion device.

FIG. 3 shows an example of the end result of transparietal occlusion achieved by the invention device.

FIG. 4 is a section view, according to FIG. 5's C-C lines, of the invention device FIG. 5 is a side view of the device inserted into a sleeve.

FIG. 6 is a section view according to the D-D lines.

FIG. 7 shows a step in the implementation of the invention device.

FIG. 8 illustrates a section view according to the E-E lines.

The occlusive device according to the invention can be used in various medical or surgical fields.

The remainder of the description shall outline more specifically an embodiment applying the occlusive device to the creation of a vascular occlusion device, along with an embodiment of the invention applying the occlusive device to valves for surgical or medical instruments.

In general terms, the invention device comprises a hollow cylindrical element 1 that can be twisted according to its axis 4, this deformation creating a striction zone advantageously widest towards the middle of the length of the hollow cylindrical element 1, although this is not limiting.

The cylindrical element can be twisted by modifying the relative angular positions of its ends.

Figure 10:
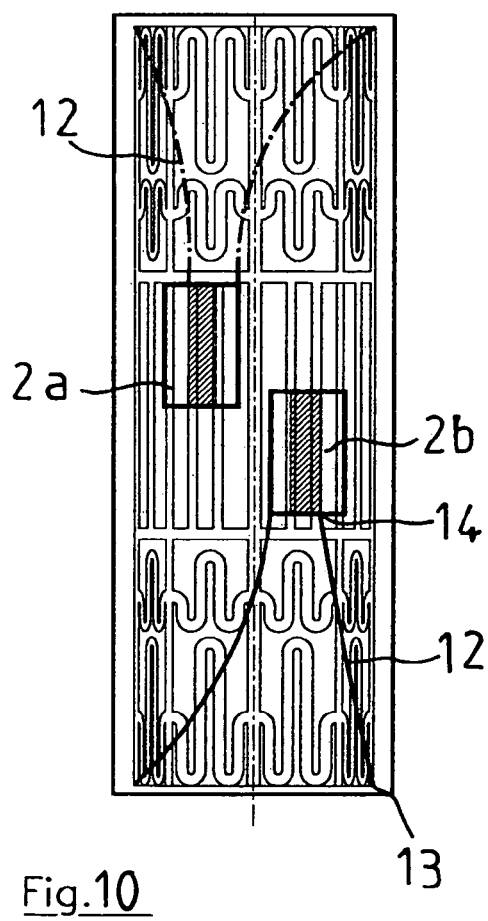
FIG. 10 is a side view of the invention device in a preferred embodiment, with obturation webs.

The occlusive device furthermore comprises two obturation elements 2a, 2b for example, presented in FIGS. 5 and 10 and integral to the inner wall of the cylindrical element 1.

The obturation elements 2a, 2b form a passage 3 through the hollow cylindrical element 1 in resting position.

Furthermore, the obturation elements 2a, 2b are advantageously integral to two distinct areas along the length of the cylindrical element 1.

FIGS. 4 and 6 show an example cross section of the obturation elements 2a, 2b, crescent moon shaped in order to form an arc shaped portion representing a wall for residual passage 3.

The obturation elements 2a, 2b may or may not be made from a polymer material with shape memory properties.

The obturation elements 2a, 2b are positioned on the inner wall of the cylindrical element 1 in such a manner that, on twisting of the cylindrical element 1, they are pressed against each other, thus blocking the passage 3.

Figure 9:
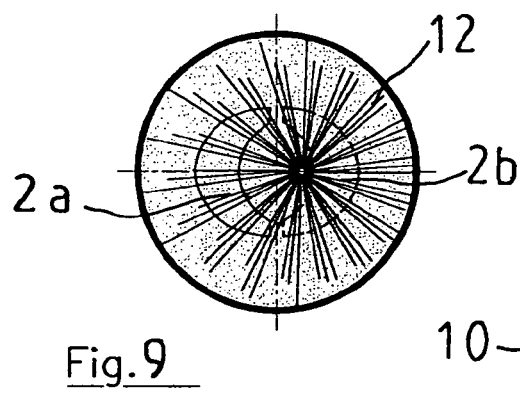
FIG. 9 is a bottom view.
Figure 11:
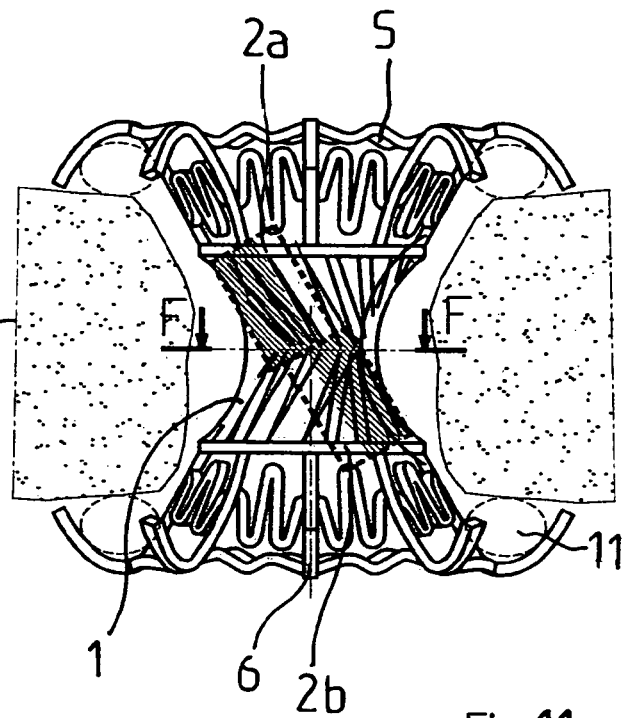
FIG. 11 illustrates a vascular occlusion device inserted through the wall of a vessel and FIG. 12 is a cross section according to the F-F lines, without the cylindrical element.

An example of a blocked position configuration is presented in FIG. 11.

Figure 12:
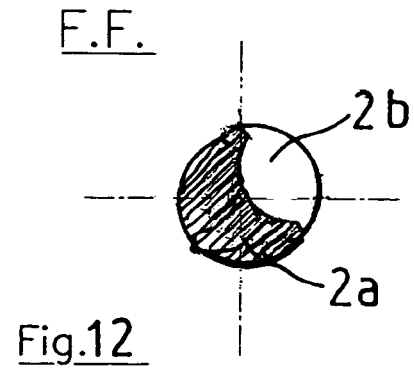

FIG. 12 clearly shows that, in this relative configuration, the obturation elements 2a, 2b are complementary in occluding the passage 3.

In the represented case, the application of two obturation elements 2a, 2b is achieved by one of their sides, or lateral surfaces, in this case oriented in a transversal manner to axis 4.

The application is therefore achieved by overlap according to axis 4 of the crescent moon shaped surfaces.

If necessary, the obturation elements 2a, 2b can be slightly compressed when placed against each other.

Furthermore, elements 2a, 2b can be arranged in such a manner that they are applied against each other over at least a portion of their longitudinal surfaces (oriented according to axis 4).

The relative position of the obturation elements 2a, 2b on the inner wall of the cylindrical element 1 is adapted according to the desired deformation of cylindrical element 1 until such point as the two obturation elements 2a, 2b are applied.

In particular, it is possible to ensure that the obturation elements 2a, 2b are diametrically opposed on the wall of the cylindrical element 1 in resting position, as shown in FIGS. 4 to 6.

A relative rotation of the two ends of the cylindrical element, of a predetermined angular amplitude brings into contact the sides of the two obturation elements 2a, 2b.

The following describes in a more precise manner an embodiment of the occlusive device for a vascular occlusion device application.

In this context, reference is made to FIGS. 1 to 12, presenting a specific embodiment of this application.

FIG. 1 shows in detail an example of structure that the cylindrical element 1 can present. In particular, element 1 may be in the form of a metallic frame, Nitinol® based for example and presenting three distinct zones. The first zone, central, constitutes the cylindrical element 1 itself and can be twisted as shown in FIGS. 2 and 3. Around the cylindrical element 1, two expanding elements 5 in the form of self-expanding frames, are represented and may be in a configuration as used in the field of endovascular prostheses. Expanding elements 5, 6 possess shape memory properties allowing them to undergo deployment deformation when released.

This release occurs through a sleeve 9 that surrounds the whole device prior to implementation by the practitioner. The cylindrical element 1 and expanding elements 5, 6 are held within the sleeve 9 in resting position.

During implantation, the practitioner progressively removes the sleeve 9 in such a manner as to release an initial expanding element to apply it against the wall of a vessel 10.

This removal can be achieved using a push element in the form of a long, hollow cylindrical element appropriate, by virtue of its width, to be applied to the edge of the occlusive device to exercise a force contrary to removal of the sleeve 9, thus immobilising the occlusive device during removal.

At this time, the vascular occlusion device is partially positioned, but expanding element 5 is still in the sleeve 9. Rotation of the sleeve 9 by the practitioner twists cylindrical element 1, thus creating a striction zone, as represented in FIG. 2.

When the desired degree of striction is achieved (this can be easily adjusted by means of the amplitude of rotation implemented by the practitioner), the other expanding element 5 is released from the sleeve 9 by sliding it out (again using a push device if necessary). This release deploys the expanding element and applies it to the vessel wall 10.

FIGS. 2 and 3 more specifically show a transparietal application of the present vascular occlusion device. In this context, it is expanding element 6 that is applied to the internal wall and expanding element 5 to the outer wall.

The sleeve 9 receives, in its inner volume, the unit comprising the cylindrical element 1 and the expanding elements 5, 6.

Furthermore, the cylindrical element 1 itself receives, in its inner volume, by attachment to its inner wall, the obturation elements 2a, 2b, which nevertheless leave a residual passage 3 according to the device's axis 4.

For example, the passage 3 can receive a guide used during handling operations.

Preferably, the seal achieved by means of the occlusive device integrated into the vascular occlusion device should be supported by additional means.

More specifically, a seal 11 may be applied to the outer periphery of at least one of the expanding elements 6. For example, an O ring seal 11, made from a sufficiently deformable material to follow the deformations of the element 6 during its deployment, may be used.

The seal 11 is applied, through this deployment, to the wall of the vessel 10.

Still in a complementary manner to an occlusive device, the vascular occlusion device may include at least one web 12, as shown in FIG. 10. In its resting position, the web 12 possesses a roughly tapered circular shape, possibly slightly bent, extending from one end 14 of the obturation element and the edge 13 of the expanding element 6 located on the same side. Such a situation is visible in FIG. 10, and in the bottom view of FIG. 9.

By establishing such a continuous web 12, a "funnel" effect is generated, thus avoiding any blood leakages out of the zone delimited by the passage 3.

When deploying the expanding element 6, the web 12 follows the corolla deformation.

Below we describe more specifically an embodiment of the occlusive device of the invention for an application to valves for surgical and medical instruments.

Figure 13:
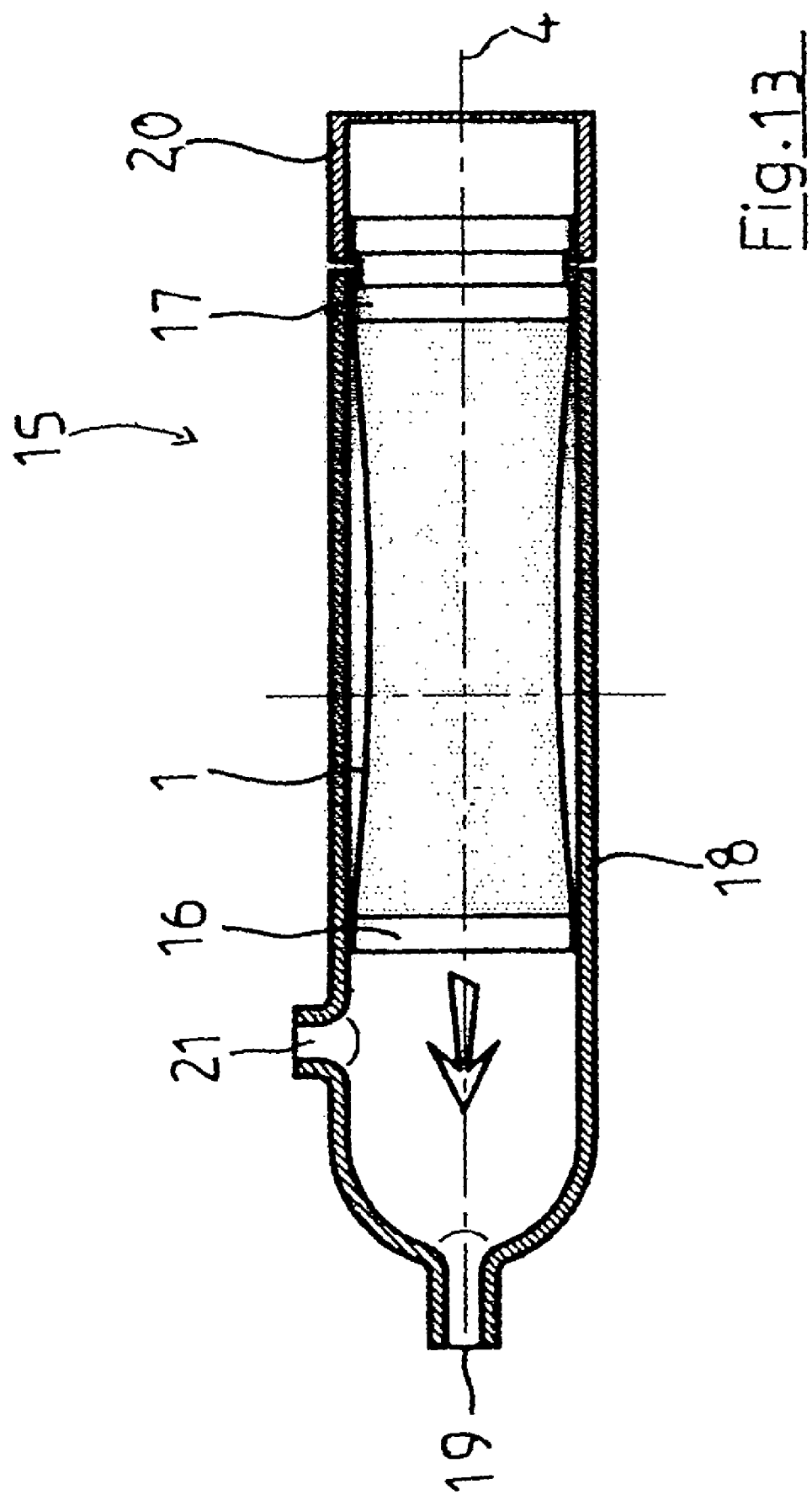
FIG. 13 shows a single valve application embodiment of the occlusive device of the invention for introducer type medical or surgical instruments.

In particular, FIG. 13 illustrates the formation of such a valve 15 that can be integrated into or added to a body introduction instrument.

For this purpose, the valve 15 comprises a shell 18 able to receive, in its inner volume, an occlusive device comprising a cylindrical element 1.

The valve 15 furthermore comprises a proximal end with an opening 19 for passing elements during introduction, along with an additional opening 21.

The distal end 20 of the valve 15 is able to receive an additional valve element and/or a simple angular control element.

According to this application, the cylindrical element 1 is surrounded by rings 16, 17, whose relative angular position can be adjusted in such a manner as to ensure the twisting of element 1.

Although not represented, element 1 receives, in its inner volume, the obturation elements 2a, 2b.

According to the example, rotation of ring 17, caused by manipulating the distal end 20 of valve 15, alters the relative angular position of rings 16, 17 and causes twisting of element 1. This twisting deformation leads to a modification of the position relative to obturation elements 2a, 2b until they are applied in such a manner as to block the passage 3.

It is thus possible to totally or partially open or close passage 3 by altering the position of ring 17, and this while ring 16 is fixed.

Of course, this embodiment is only an example and other variants may be considered.

In particular, ring 16 may be free to rotate, while ring 17 could be fixed. Furthermore, the rings may additionally be moved together or apart, for example by means of a helicoidal runner type link between the housing 18 of the valve 15 and the ring 17.

In the context of this application, the cylindrical element 1 comprises a sealed wall and may be made, in particular, from a woven (or not) textile material, or from a polymeric material such as P.T.F.E. (Poly Tetra Fluoro Ethylene).

| REFERENCES | |
|---|---|
| 1. | Cylindrical element |
| 2a, 2b. | Obturation elements |
| 3. | Passage |
| 4. | Axis |
| 5. | Expanding element |
| 6. | Expanding element |
| 9. | Sleeve |
| 10. | Vessel wall |
| 11. | Seal |
| 12. | Web |
| 13. | Edge |
| 14. | End of obturation element |
| 15. | Valve |
| 16. | Ring |
| 17. | Ring |
| 18. | Housing |
| 19. | Opening |
| 20. | Distal end |
| 21. | Opening |

The invention claimed is:

1. Occlusive device for medical or surgical use, comprising:
    a hollow cylindrical element (1) configured to be twisted according to an axis of said cylindrical element to create a striction zone,
    said cylindrical element having two obturation elements (2a, 2b) located within an internal volume of said cylindrical element and integral to an inner wall of said cylindrical element (1), the two obturation elements (2a, 2b) forming a passage (3) in a first mode, and the two obturation elements (2a, 2b) configured to press against each other to block the passage (3) in a second mode upon the cylindrical element (1) being twisted.

2. Device according to claim 1, wherein
    the two obturation elements (2a, 2b) are integral to two distinct areas of the length of the cylindrical element (1).

3. Device according to claim 1, wherein the obturation elements (2a, 2b) have a crescent-shaped cross section.

4. Device according to claim 1, wherein the two obturation elements (2a, 2b) are integral to two diametrically opposed areas of a wall of the cylindrical element (1).

5. Device according to claim 1, wherein the obturation elements (2a, 2b) are made from a polymeric material.

6. Device according to claim 1, further comprising:
    two end parts, surrounding the cylindrical element (1), an angular position of the two end parts defining a torsion of said cylindrical element (1).

7. Device according to claim 1, wherein the cylindrical element (1) has a circular cross section.

8. Device according to claim 1, wherein the obturation elements (2a, 2b) are applied one against each other by means of one of lateral surfaces of the obturation elements.

9. Vascular occlusion device, comprising:
    an occlusive device according to claim 1.

10. Device according to claim 9, further comprising:
    two end parts, surrounding the cylindrical element (1), a relative angular position of said two end parts determining a torsion of said cylindrical element (1), and said two end parts having means to attach to a wall of a vessel.

11. Device according to claim 10, wherein the the means to attach to a wall of a vessel are expanding elements (5, 6).

12. Device according to claim 11, further comprising:
    a seal (11) on an outer surface of at least one of the expanding elements (5, 6), said seal (11) configured for application to the wall of the vessel.

13. Device according to claim 11, further comprising:
    a peripheral obturation web (12) extending from one end of at least one obturation element and an edge (13) of a corresponding expanding element (5, 6).

14. Device according to claim 9, further comprising:
    a removable guide (7) positioned according to the axis (4) of the cylindrical element (1) and crossing the passage (3).

15. Device according to claim 14, further comprising:
    a removable sheath (8) between a wall of the obturation elements (2a, 2b) and an external wall of the guide (7).

16. Device according to claim 9, further comprising:
    a removable sleeve (9) surrounding the occlusive device.

17. Valve (15) for surgical or medical instrument, comprising:
    a closeable passage; and
    an occlusive device according to claim 1.

18. Valve (15) according to claim 17, wherein the cylindrical element (1) is configured to be twisted by means of two rings (16, 17), each of the two rings being integral to one end of the cylindrical element (1).

* * * * *